(12) United States Patent
Rodan et al.

(10) Patent No.: US 9,144,434 B1
(45) Date of Patent: Sep. 29, 2015

(54) METHODS AND COMPOSITIONS FOR TREATING SKIN

(75) Inventors: Katie Rodan, Oakland, CA (US); Kathy Fields, San Francisco, CA (US)

(73) Assignee: Rodan & Fields, LLC, San Francisco, CA (US)

(*) Notice: Subject to any disclaimer, the term of this patent is extended or adjusted under 35 U.S.C. 154(b) by 0 days.

(21) Appl. No.: 13/248,367

(22) Filed: Sep. 29, 2011

Related U.S. Application Data

(60) Provisional application No. 61/387,577, filed on Sep. 29, 2010.

(51) Int. Cl.
*A61B 17/3205* (2006.01)
*A61B 17/00* (2006.01)

(52) U.S. Cl.
CPC ... *A61B 17/3205* (2013.01); *A61B 2017/00761* (2013.01)

(58) Field of Classification Search
CPC ............... A61M 2037/0046; A61M 37/0015; A61H 2201/1695; A61H 15/02; A61B 2017/00761; A61B 17/3205
USPC ............ 606/131, 186, 189, 201, 204; 601/94, 601/95, 118–120, 122–125, 128, 129; 424/59, 78.03, 78.06; 514/18.6, 18.8
See application file for complete search history.

(56) References Cited

U.S. PATENT DOCUMENTS

| | | | |
|---|---|---|---|
| 5,554,102 A | 9/1996 | Chiou | |
| 5,741,219 A | 4/1998 | Schweisfurth | |
| 5,782,802 A | 7/1998 | Landau | |
| 5,964,729 A | 10/1999 | Choi et al. | |
| 6,702,766 B2 | 3/2004 | Guitay | |
| 7,559,944 B2 | 7/2009 | Whang | |
| 7,658,728 B2 | 2/2010 | Yuzhakov | |
| 7,819,828 B2 | 10/2010 | Anderson | |
| 7,850,985 B2 | 12/2010 | Patel et al. | |
| 8,048,019 B2 | 11/2011 | Nisato et al. | |
| 8,283,314 B1 * | 10/2012 | Marini | 514/8.9 |
| 8,353,871 B2 | 1/2013 | Zimmerman et al. | |
| 8,376,984 B2 | 2/2013 | James | |
| 8,414,548 B2 | 4/2013 | Yuzhakov | |
| 8,470,356 B2 | 6/2013 | Patel et al. | |
| 8,540,678 B2 | 9/2013 | Kodgule et al. | |
| 8,721,574 B2 | 5/2014 | Han | |
| 2004/0106894 A1 | 6/2004 | Hunter et al. | |
| 2004/0220551 A1 | 11/2004 | Flaherty et al. | |
| 2005/0203575 A1 | 9/2005 | Carson et al. | |
| 2006/0051404 A1 | 3/2006 | Yeshurun et al. | |
| 2006/0253079 A1 | 11/2006 | McDonough et al. | |
| 2007/0088264 A1 | 4/2007 | Liebl | |
| 2008/0154161 A1 | 6/2008 | Abbott | |
| 2008/0161735 A1 | 7/2008 | Lee et al. | |
| 2008/0248079 A1 | 10/2008 | Dempsey et al. | |

(Continued)

FOREIGN PATENT DOCUMENTS

| | | | | |
|---|---|---|---|---|
| WO | WO 02/49711 | * | 6/2002 | ............ A61M 37/00 |
| WO | WO2005/110525 A2 | | 11/2005 | |

(Continued)

*Primary Examiner* — Thomas McEvoy
(74) *Attorney, Agent, or Firm* — Merchant & Gould P.C.

(57) ABSTRACT

The present disclosure generally relates to methods and compositions for treating skin. In some embodiments, the method uses an exfoliation tool. In some embodiments, the method uses an exfoliation tool together with selected skin care agents or compositions.

6 Claims, 2 Drawing Sheets

(56) References Cited

U.S. PATENT DOCUMENTS

| | | |
|---|---|---|
| 2009/0118698 A1* | 5/2009 | Liebl .............................. 604/506 |
| 2009/0312691 A1* | 12/2009 | Kim et al. ....................... 604/22 |
| 2010/0042050 A1 | 2/2010 | Chowdhury |
| 2010/0068161 A1* | 3/2010 | Todary ............................ 424/59 |
| 2010/0121307 A1 | 5/2010 | Lockard et al. |
| 2010/0256594 A1 | 10/2010 | Kimmell et al. |
| 2010/0262081 A1 | 10/2010 | Lee et al. |
| 2011/0009782 A1* | 1/2011 | Pampalone et al. ........... 601/119 |
| 2011/0172610 A1 | 7/2011 | Kodgule et al. |
| 2011/0218497 A1 | 9/2011 | Assaf |
| 2011/0230804 A1 | 9/2011 | Serhan |
| 2011/0319865 A1 | 12/2011 | Buss |
| 2012/0238925 A1 | 9/2012 | Winkley |
| 2012/0265106 A1 | 10/2012 | Accardo et al. |
| 2013/0150826 A1 | 6/2013 | Almohizea |
| 2013/0218083 A1 | 8/2013 | Yuzhakov |
| 2013/0226140 A1 | 8/2013 | Kodgule et al. |
| 2014/0066846 A1 | 3/2014 | Genosar |
| 2014/0066902 A1 | 3/2014 | Kodgule et al. |

FOREIGN PATENT DOCUMENTS

| | | |
|---|---|---|
| WO | WO2008/125798 A1 | 10/2008 |
| WO | WO2012/006259 A1 | 1/2012 |
| WO | WO2013/076715 A1 | 5/2013 |
| WO | WO2013/084189 A2 | 6/2013 |

* cited by examiner

//www.w3.org/1999/xhtml">
METHODS AND COMPOSITIONS FOR TREATING SKIN

CROSS-REFERENCE TO RELATED APPLICATIONS

This application claims benefit to U.S. Provisional Application Ser. No. 61/387,577 filed on Sep. 29, 2010, which application is incorporated herein by reference.

FIELD

The present disclosure generally relates to methods and compositions for treating skin. In some embodiments, the method uses an exfoliation tool. In some embodiments, the method uses an exfoliation tool together with selected skin care agents or compositions.

BACKGROUND

Proper skin care is important for heath and cosmetic reasons. Skin is a vital organ and a breakdown in the skin can adversely affect the skin's function as a barrier and make it susceptible to infection. A breakdown in the skin can also be very painful, such as the case of excessive dry skin. Visual irregularities in the skin can adversely affect a person's confidence and other people's perceptions.

There remains a need for improved methods of treating skin and maintaining or improving its health and cosmetic features. It is against this background that the present disclosure is made.

SUMMARY

Surprisingly, it has been found that using an exfoliation tool together with selected skin care agents results in improved skin health and appearance.

Accordingly, in some embodiments, the present disclosure relates to a method of treating skin where a user applies a first skin care agent to skin and treats the skin with an exfoliation tool. In some embodiments, the method also includes additional skin care agents. In some embodiments, the method uses a specific treatment regimen.

In some embodiments, the present disclosure relates to a kit that includes an exfoliation tool and selected skin care agents. The kit can also include specific instructions that explain how to use the exfoliation tool and selected skin care agents.

Finally, in some embodiments, the present disclosure relates to methods of treating skin using an exfoliation tool and selected skin care compositions.

These and other embodiments will be apparent to those of skill in the art and others in view of the following detailed description. It should be understood, however, that this summary, and the detailed description illustrate only some examples of various embodiments, and are not intended to be limiting to the claimed invention.

DETAILED DESCRIPTION

The present disclosure generally relates to skin treatment using an exfoliation tool and selected skin care agents. While not wanting to be bound by theory, it is believed that the combination of the exfoliation tool and the selected skin care agents increases the uptake of the selected skin care agents by the epidermis (outer layer of skin) than if the skin care agent was just placed on top of the epidermis. This is believed to be in part because the exfoliation tool increases the surface area of the epidermis by creating micro pores or holes in the skin, thereby allowing a greater number of skin cells on the epidermis to contact and benefit from the selected skin care agent. One result of this is that a user can see improved results in a shorter period of time.

The Exfoliation Tool

Figure 1:
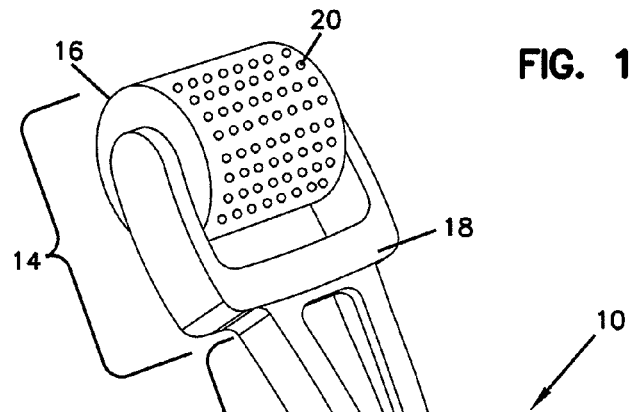
FIG. 1 shows a view of the exfoliation tool.

The exfoliation tool of the present disclosure is designed to create micro pores, channels, or holes in the epidermis or outer layer of the skin. In some embodiments, the exfoliation tool is a roller attached to a handle or wand, such as that shown in FIG. 1. FIG. 1 generally shows an exfoliation tool 10. The exfoliation tool 10 includes a handle or wand 12 and a head 14 attached to the handle 12. The head 14 includes a roller 16. The roller 16 is held in place by a U-shaped collar 18 that is attached to the handle or wand 12 and engages the roller 16 at either end in such a way that allows the roller 16 to rotate. The roller 16 includes a plurality of acupuncture needles 20. FIG. 1 shows the acupuncture needles 20 in rows, but it is understood that the needles may be arranged in a variety of configurations. The exfoliation tool 10 is preferably easily manufactured. In some embodiments, the handle 12, head 14, including the collar 18 and the roller 16 are injection molded plastic. The acupuncture needles 20 are preferably stainless steel, and more preferably surgical grade stainless steel.

Figure 2:
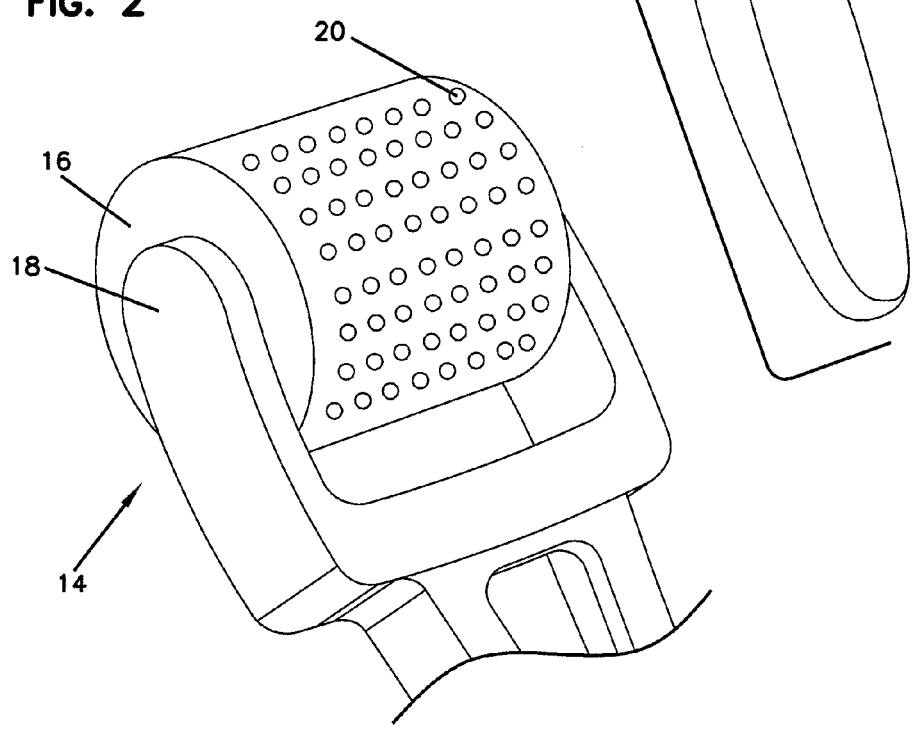
FIG. 2 shows a close up of the exfoliation tool head, including the roller and the acupuncture needles.

FIG. 2 shows a close up of the head 14, including the collar 18, roller 16, and acupuncture needles 20. The acupuncture needles 20 preferably form micro holes, pores, or channels in the epidermis of the skin. It is understood that other structures may be used instead of acupuncture needles. When using acupuncture needles, the needles are preferably solid and made of stainless steel. The needles are preferably from about 0.1 mm to about 0.5 mm in length so that when the exfoliation tool is placed on skin and rolled using moderate pressure, the needles penetrate only the epidermis, and not the deeper layers of skin. In some embodiments, the needles do not penetrate more than about 100 microns to 500 microns into the epidermis.

Figure 3:
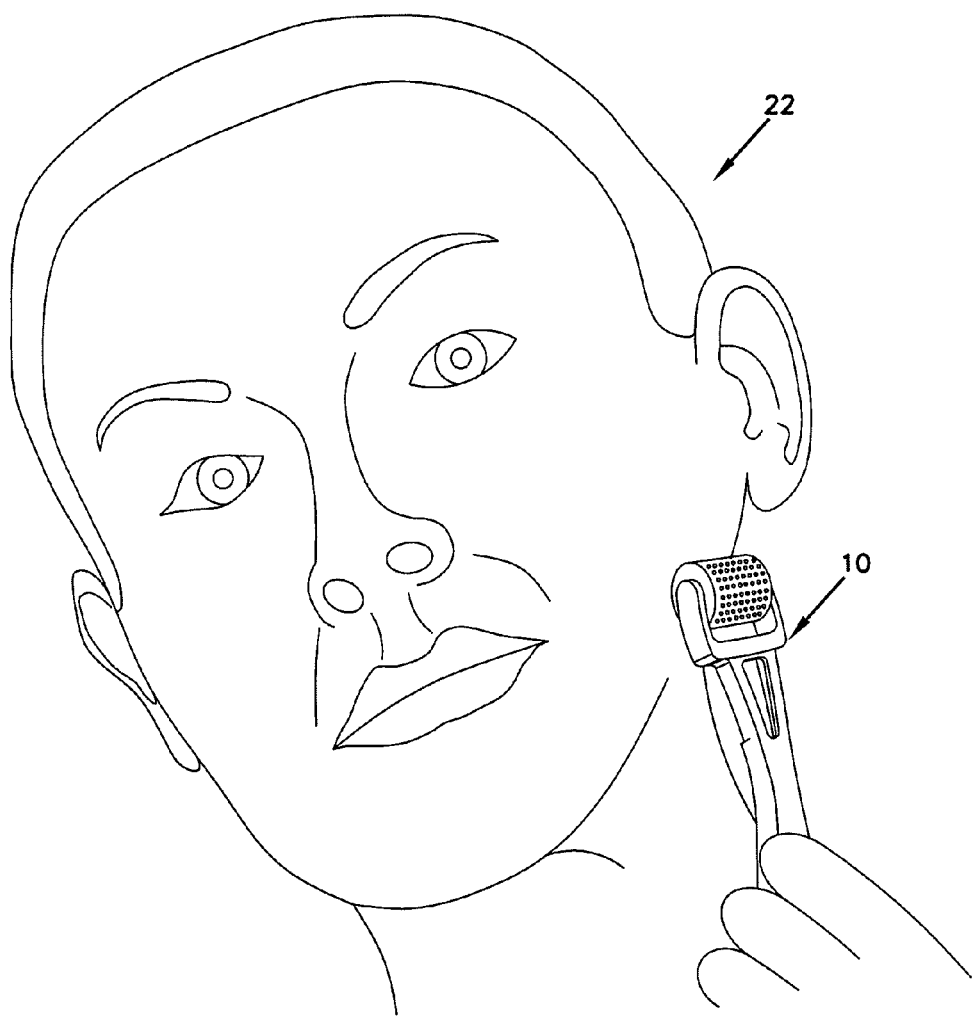
FIG. 3 shows a person using the exfoliation tool on their face.

FIG. 3 shows a person 22 using the exfoliation tool of FIG. 1 on their face. In some embodiments, the exfoliation tool can be scaled slightly smaller for use on the face or slightly larger for use on the body or scalp, reflecting the respective differences in surface area of the face versus the rest of the body or scalp. During use on the face, it may be beneficial to divide the face into sections such as the forehead, right side, left side, chin, and neck. A user may then roll the head of the exfoliation tool of FIG. 1 over each section using moderate pressure. In some embodiments, it may be beneficial for the user to change the rolling direction with each pass. A similar method can be used when treating other body parts or the scalp (i.e., dividing into sections and rolling the exfoliation tool over the various sections, changing the rolling direction from time to time).

Selected Skin Care Agents

The exfoliation tool may be used in conjunction with at least one skin care agent. The skin care agent is preferably an agent that helps maintain, treat, or improve the health or cosmetic appearance of skin. Exemplary skin care agents include the following: abrasives, antiacne agents, antidandruff agents, antifungal agents, antimicrobial agents, antioxidants, toners, moisturizers, skin conditioners, humectants, emollients, skin bleaching or lightening agents, proteins, cleaners, hair conditioners, and the like.

Abrasives may be used to remove unwanted skin such as dead skin cells and calluses. Exemplary abrasives include but are not limited to the following: alumina, aluminum silicate, apricot seed powder, attapulgite, avocado powder, bamboo powder, barley flour, bentonite, calcium carbonate, calcium phosphate, calcium pyrophosphate, calcium sulfate, chalk, chitin, coconut shell powder, colloidal oatmeal, comfrey leaf powder, corn cob meal or powder, corn flour, corn meal, corn starch, diamond powder, diatomaceous earth, dicalcium phosphate, dicalcum phosphate dehydrate, egg shell powder, Fuller's earth, hydrated silica, hydroxyapatite, kaolin, kiwi seed, lauryl acrylate polymers, loess, magnesium potassium fluorosilicate, magnesium trisilicate, microcrystalline cellulose, montmorillonite, Moroccan lava clay, oat bran, oat flour, oatmeal, oyster shell powder, peach pit powder, peanut flour, pecan shell powder, polyethylene, pumice, raspberry seed, rice bran, rye flour, sand, silica, sodium bicarbonate, sodium hydroxypropyl starch phosphate, sodium magnesium fluorosilicate, sodium silicoaluminate, soybean flour, sweet almond meal, talc, tin oxide, tricalcium phosphate, walnut shell powder, wheat bran, wheat flour, wheat powder, wheat starch, wood powder, zirconium silicate, and derivatives and combinations of these.

Antiacne agents may be used to treat blemishes, pimples, blackheads, and whiteheads. Exemplary antiacne agents include but are not limited to salicylic acid, benzoyl peroxide, or sulfur, and their derivatives and combinations.

Antidandruff agents may be used to treat dandruff, seborrheic dermatitis, or psoriasis. Exemplary antidandruff agents include but are not limited to the following: coal tar, salicylic acid, selenium sulfide, sulfur, zinc pyrithione, and their derivatives and combinations.

Antifungal agents include agents that inhibit the growth and reproduction of fungal cells or decreases the number of fungi present. Exemplary antifungal agents include but are not limited to the following: calcium undecylenate, ketoconazol, povidone-iodine (PVP-iodine), tea tree oil, undecylenic acid, zinc undecylenate, and their derivatives and combinations.

Antimicrobial agents include agents that kill microorganisms or prevent or inhibit microorganism growth and reproduction or agents that help prevent infection in minor cuts, scrapes, and burns. Exemplary antimicrobial agents include but are not limited to the following: lower chain ($C_1$-$C_4$) alcohols, quaternary ammonium compounds such as benzalkonium chloride and benzethonium chloride, clindamycin, methylbenzethonium chloride, hydrogen peroxide, Oligopeptide-10, phenols, tea tree oil, triclosan, povidone-iodine (PVP-Iodine), and their derivatives and combinations.

Antioxidants include agents that are characterized as free radical scavengers and help reverse skin damage caused by free radicals. Exemplary antioxidants include but are not limited to the following: acetyl cysteine, alpha lipoic acid, arbutin, ascorbic acid (vitamin C), ascorbic acid polypeptide, ascorbyl dipalmitate, ascorbyl methylsilanol pectinate, ascorbyl palmitate, ascorbyl stearate, BHA, BHT, t-butyl hydroquinone, caffeic acid, camellia sinensis oil, carotenoids, chitosan ascorbate, chitosan glycolate, chitosan salicylate, chlorogenic acids, CoQ10, cortisen, cysteine, cysteine HCl, decyl mercaptomethylimidazole, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, diosmine, disodium ascorbyl sulfate, disodium rutinyl disulfate, distearyl thiodipropionate, ditridecyl thiodipropionate, dodecyl gallate, dunaliella salina extract, erythorbic acid, ethyl ferulate, ferulic acid, hydroquinone, p-hydroxyanisole, hydroxylamine HCl, hydroxylamine sulfate, hydroxytyrosol, isooctyl thioglycolate, isoquercitrin, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycloic acid, phloroglucinol, potassium ascorbyl tocopheryl phosphate, potassium sulfite, propyl gallate, resveratrol, rosmarinic acid, rutin, sirtunis, sodium ascorbate, sodium ascorbyl/cholesteryl phosphate, sodium bisulfite, sodium erythorbate, sodium metabisulfite, sodium sulfite, sodium thioglycolate, sorbityl furfural, tea tree oil, tetrahexyldecyl ascorbate, tetrahydrodiferuloylmethane, thiodiglycol, thiodiglycolamide, thiodiglycolic acid, thioglycolic acid, thiolactic acid, thiosalicylic acid, thiotaurine, tocophereth derivatives, tocopherol (vitamin E), tocophersolan, tocopheryl acetate, tocopheryl linoleate, tocopherol linoleate/oleate, tocopheryl nicotinate, tocopheryl succinate, tocoquinone, o-tolyl biguanide, tri(nonylphenyl)phosphate, ubiquinone, vitamin D, zinc dibutyldithiocarbamate, and their derivatives and combinations.

Toners include agents that create a tightening or tingling sensation on skin. Exemplary toners include but are not limited to the following: alcohol derivatives such as denatured alcohol and SD alcohol, aluminum derivatives such as aluminum acetate, aluminum bromohydrate, aluminum chloride, aluminum chlorohydrex, aluminum citrate, aluminum diacetate, aluminum dichlorohydrate, aluminum dichlorohydrex, aluminum glycinate, aluminum lactate, aluminum phenolsulfonate, aluminum sesquichlorohydrate, aluminum sesquichlorohydrex, and aluminum sulfate, aluminum zirconium derivatives such as aluminum zirconium octachlorohydrex, aluminum zirconium pentachlorohydrate, aluminum zirconium pentachlorohydrex, aluminum zirconium tetrachlorohydrate, aluminum zirconium tetrachlorohydrex, aluminum zirconium trichlorhydrate, and aluminum zirconium trichlorohydrex, ammonium alum, calcium chloride, calcium lactate, dimethyl MEA, gallic acid, lens esculenta (lentil) seed extract, potassium alum, sodium alum, sodium aluminum chlorohydroxy lactate, sodium aluminum lactate, tannic acid, tioxolone, tranexamic acid, zinc acetate, zinc chloride, zinc lactate, zinc phenolsulfonate, zinc sulfate, zirconium chlorohydrate, witch hazel, and their derivatives and combinations.

Skin conditioning agents or moisturizers can be classified into different groups such as emollients, humectants, and occlusive agents. Emollients include agents that remain on the upper layers of skin and act as lubricants and improve appearance. Exemplary emollients include but are not limited to the following: lanolin, glycerides, fruit oils, nut oils, vegetable oils, dimethicones, methicone, cyclomethicone, dormin, fatty acids, myristate derivatives like butyl myristate and myristyl myristate, oleate derivates, $C_1$-$C_4$ glycols, fatty acid glycols, glycol esters, glycerine, glycerols, paraffin, rapeseed oil, long chain alcohols, olive oil, jojoba oil, castor oil, and their derivatives and combinations. Humectants include agents that increase the water content of the top layer of skin. Exemplary humectants include but are not limited to the following: allatoin, agarose, arginine, benzyl hyaluronate, chitosan, copper, corn glycerides, gluconolactone, lactic acid, lactobionic acid, lactose, lysine, kombucha, maltitol, maltose, mannitol, propylene glycol, sodium aspartate, fructose, honey, glycerin, hydroxyethyl urea, and their derivatives and combinations. Occlusive agents slow the evaporation of water from skin. Exemplary occlusive agents include but are not limited to the following: petrolatum, shea butter, dimethicones, plant and animal oils such as avacodo, canola, cod liver, and corn, mineral oil, olive oil, soybean oil, lanolin, glycerides, beeswax, triglycerides, long chain fatty alcohols, coco butter, coconut oil, jojoba oil, propylene glycol and their derivatives and combinations.

In addition to skin conditioning agents that provide a moisturizing benefit, there are other skin conditioning agents that improve the appearance of skin. Exemplary skin conditioning agents include but are not limited to the following: cholesterol, cystine, hyaluronic acid, keratin, egg yolk, glycine, gluconolactone, lactic acid, lactobionic acid, panthenol, retinol, salicylic acid, vegetable oil, proteins, vitamins, bisabolol, ceramide, coenzyme A, lecithin and their derivatives and combinations.

Skin bleaching or lightening agents include agents that lighten pigment in skin. The preferred skin bleaching agent is hydroquinone. Brighteners include but are not limited to azelaic acid, bearberry, deoxyarbuten, glycyrrhiza glabra (Licorice) root extract, kojic acid, peat extract, and their derivatives and combinations.

Proteins include animal, plant, fungi, yeast, and bacteria proteins that have skin health benefits. Exemplary proteins include but are not limited to the following: collagen, keratin, soy protein, wheat protein, bean palmitate, ascorbic acid polypeptide, the amino acids, casein, cholecalciferol polypeptide, rice protein, silk protein, gluten protein, lysine, acetyl glucosamine, actin, actizyme, albumen, conchiorin protein, corn protein, egg protein, elastin, fibronectin, gadidae protein, hemoglobin, hexapeptide-21, lactalalbumin, lupine protein, maple sycamore protein, milk protein, myristoyl pentapeptide-8, myristoyl tetrapeptide-8, oat protein, oligopeptide 10, palmitoyl hexapeptide-14, palmitoyl oligopeptide, palmitoyl tetrapeptide-7, pea protein, potato protein, reticulin, rice bran protein, serum protein, sweet almond protein, tetrapeptide-16, vegetable protein, yeast protein, palmitoyl oligopeptide, pantothenic acid polypeptides, milk solids, sericin, albumen, amylase, amyloglucosidase, arginine, bromelain, catalase, gelatin, zein, crystallins, cytochrome C, deoxyribonuclease, gliadin, glucose oxidase, glycoproteins, lactoferrin, lactoglubulin, lactoperoxidase, lipase, nisin, oxido reductases, papain, pepsin, subtilisin, sutilains, and their combinations and derivatives.

Cleansers include agents that are used for cleaning the skin and hair by solubilizing oil and suspending soils. Cleansers may be foaming or non-foaming. Exemplary cleaners are typically a surfactant and can be characterized as nonionic, anionic, or zwitterionic.

Nonionic Surfactants.

Nonionic surfactants are generally characterized by the presence of an organic hydrophobic group and an organic hydrophilic group. The length of the hydrophilic moiety can be readily adjusted to yield a water dispersible or water soluble compound having the desired degree of balance between hydrophilic and hydrophobic properties. Exemplary nonionic surfactants include the following:

Alkylpolysaccharide surfactants that include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. Exemplary alkylpolysaccharide surfactants include caproyl ethyl glucoside, caprylyl/capryl glucoside, coco-glucoside, deceth-7 glucoside, decyl glucoside, Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range.

Condensation products of one mole of saturated or unsaturated, straight or branched chain carboxylic acid having from about 8 to about 18 carbon atoms with from about 6 to about 50 moles of ethylene oxide. The acid can be a mixture of acids in the above defined carbon atoms range or it can be an acid having a specific number of carbon atoms within the range.

Amine oxides are tertiary amine oxides and semi-polar nonionic surfactants corresponding to the general formula:

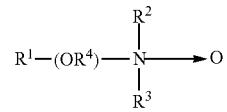

where the arrow=a conventional representation of a semi-polar bond; and, $R^1$, $R^2$, and $R^3$ may be aliphatic, aromatic, heterocyclic, alicyclic, or combinations thereof.

Useful amine oxide surfactants are almondamidopropylamine oxide, babassuamidopropylamine oxide, behenamine oxide, cocamidopropyle amine oxide, cocamine oxide, decylamine oxide, decyltetradecylamine oxide, dihydroxyethyl alkoxyalkylamine oxides, dihydroxyalkyl alkylamine oxides, hydrogenated palm kernel amine oxide, hydrogenated tallowamine oxide, alkoxy alkylamine oxides, isostearamidopropylamine oxide, isostearamidopropyl morpholine oxide, lauramidopropylamine oxide, lauramine oxide, methyl morpholine oxide, milkamidopropyl amine oxide, minkamidopropylamine oxide, myrstamidopropylamine oxide, myrstamine oxide, myristyl/cetyl amine oxide, oleamidopropylamine oxide, oleamine oxide, olivamidopropylamine oxide, palmitamidopropylamine oxide, palmitamine oxide, sesamidopropylamine oxide, soyamidopropylamine oxide, stearamidopropylamine oxide, stearamine oxide, tallowamidopropylamine oxide, tallowamine oxide, undecylenamidopropylamine oxide, wheat germamidopropylamine oxide.

Anionic Surfactants.

Anionic surfactants includes those with a negative charge on the hydrophobic group or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Cations (counter ions) associated with these polar groups include sodium, lithium, potassium, ammonium, substituted ammonium, calcium, barium, and magnesium.

Anionic surfactants can be subdivided into five major chemical classes: (1) acylamino acids (and salts), such as acylgluamates, acyl peptides, sarcosinates (e.g. N-acyl sarcosinates), taurates (e.g. N-acyl taurates and fatty acid amides of methyl tauride), and the like; (2) carboxylic acids (and salts), such as alkanoic acids (and alkanoates), ester carboxylic acids (e.g. alkyl succinates), ether carboxylic acids, and the like; (3) phosphoric acid esters and their salts; (4) sulfonic acids (and salts), such as isethionates (e.g. acyl isethionates), alkylaryl sulfonates, alkyl sulfonates, sulfosuccinates (e.g. monoesters and diesters of sulfosuccinate), and the like; and (5) sulfuric acid esters (and salts), such as alkyl ether sulfates, alkyl sulfates, and the like. Exemplary anionic surfactants include the following:

Linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside (the nonionic nonsulfated compounds being described herein). Exemplary alkyl sulfates include ammonium alkyl sulfates, ammonium cocomonoglyceride sulfates, ammonium dimethicone copolyol sulfate, ammonium laureth sulfates, ammonium lauryl sulfates, ammonium myristyl sulfates, ammonium palm kernel sulfate, diethylamine laureth sulfate, hydroxyethylbutylamine laureth sulfate, magnesium coco-sulfate, magnesium laureth sulfate, monoethanolamine and triethanolamine salts of coco, laureth, and $C_{10}$-$C_{15}$ alkyl sulfates, potassium lauryl sulfate, sodium $C_{12}$-$C_{20}$ alkyl sulfates, sodium laureth sulfates, sodium lauryl sulfate, sodium myristyl sulfate, sodium oleth sulfate, sodium stearyl sulfate, and sodium tallow sulfate.

Ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from 5 to 18 carbon atoms in the alkyl group in a straight or branched chain, e.g., the salts of alkyl benzene sulfonates, such as ammonium dodecylbenzenesulfonate.

Anionic carboxylate surfactants such as alkyl ethoxy carboxylates, the alkyl polyethoxy polycarboxylate surfactants and the soaps (e.g. alkyl carboxyls). Exemplary carboxylate surfactants include magnesium laureth carboxylate, monoethanolamine laureth carboxylate, sodium laureth carboxylates, sodium pareth carboxylates, sodium cocoamide carboxylates, and sodium trideceth carboxylates.

Olefin sulfonates, such as long chain alkene sulfonates, long chain hydroxyalkane sulfonates or mixtures of alkenesulfonates and hydroxyalkane-sulfonates, sulfosuccinates, alkyl sulfates, alkyl poly(ethyleneoxy) ether sulfates and aromatic poly(ethyleneoxy) sulfates. Exemplary sulfonates include DEA-methylmyristate sulfonate, magnesium lauryl hydroxypropyl sulfonate, and the like. Exemplary sulfosuccinates include ammonium lauryl sulfosuccinates, diammonium lauryl sulfosuccinates, dioctyl sodium sulfosuccinate, disodum cetearyl sulfosuccinate, disodium cocamido sulfosuccinates, disodium coco-glucoside sulfosuccinate, disodium dimethicone copolyol sulfosuccinate, disodium hydrogenated cottonseed glyceride sulfosuccinate, disodium isostearyl sulfosuccinate, disodium laureth sulfosuccinates, and the like.

Exemplary sarcosinates include sodium $C_{12}$-$C_{18}$ sarcosinates, sodium cocoyl sarcosinate, and the like. Exemplary taurates include sodium salts of cocoyl taurate, lauroyl taurate, myristoyl taurate, palmitoyl taurate, and stearoyl taurate.

Zwitterionic Surfactants.

Zwitterionic surfactants generally contain cationic and anionic groups which ionize to a nearly equal degree in the isoelectric region of the molecule and which can develop strong "inner-salt" attraction between positive-negative charge centers.

Zwitterionic surfactants include betaines of the general structure:

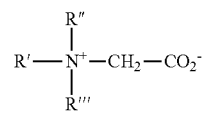

Examples of suitable betaines include almondamidopropyl betaine, apricotamidopropyl betain, avocadamidopropyl betaine, babassuamidopropyl betaine, behenamidopropyl betaine, behenyl betaine, canolamidopropyl betaine, cocamidoethyl betaine, cocamidopropyl betaine, coco-betaine, coco/oleamidopropyl betaine, decyl betaine, lauramidopropyl betaine, myristamidopropyl betaine, myristyl betaine, oleamidopropyl betaine, oleyl betaine, palmamidopropyl betaine, olivamidopropyl betaine, stearyl betaine, and the like.

Preferred cleansers include taurates, sulfates, sulfonates, carboxylates, sulfosuccinates, and sarcosinates, zwitterionic betaines, fatty acid and fatty alcohol derivatives, and alkylpolyglucoside and amine oxide surfactants. In some embodiments, the cleansers may be combined with some abrasives such as clays and sulfurs to provide light exfoliation.

Hair conditioners include agents that enhance the appearance and feel of hair by improving a property like gloss, texture, or body. Exemplary hair conditions include but are not limited to the following: lanolin, silicone, dimethicone, proteins such as amino acids, collagen, and keratin, vitamins, betaine surfactants, amine oxide surfactants, ceramide, fatty acids, eggs, milk, natural plant and animal oils, mineral oil, olive oil, polyquaternium, and their derivatives and combinations.

The skin care agents may be delivered to the skin individually or in a variety of compositions. For example, the skin care agents may be part of a water-thin liquid, thickened liquid, lotion, cream, gel, emulsion or structured liquid, paste, wax, or solid composition. When formulated as a composition, the skin care agents may be present with other skin care agents or additional ingredients that impart a skin care benefit or help in applying the skin care agent. Exemplary additional ingredients include anticaking agents, antifoaming agents, binders, buffers and pH adjusters, dyes, essential oils, and fragrances, chelating agents, corrosion inhibitors, emulsifiers, emulsion stabilizers, film formers, plasticizers, preservatives, propellants, solvents, foaming agents, hydrotropes, UV light absorbers, thickeners, and the like. When the skin care agents are combined with these additional ingredients, they can form exemplary compositions such as shampoos, conditioners, treatments, cleansers, soaps, toners, lotions, moisturizers, masks, serums, gels, scrubs, exfoliants, and wax blocks.

In some embodiments, the skin care agent or skin care compositions are available to users as over-the-counter ("OTC") products, meaning that they are available to users without a doctor's prescription. In some embodiments, the skin care agent or skin care compositions are available to users through a doctor's prescription.

A preferred skin care composition includes a combination of proteins, skin conditioners, moisturizers, and antioxidants. Exemplary proteins include sericin, collagen, keratin, amino acids, hexapeptide-21, myristoyl pentapeptide-8, myristoyl tetrapeptide-8, oligopeptide 10, palmitoyl hexapeptide-14, palmitoyl oligopeptide, palmitoyl tetrapeptide-7, tetrapeptide-16, and derivatives and combinations thereof. Exemplary skin conditioners include hyaluronic acid, alpha hydroxyl acids (ie: glycolic acid, lactic acid, ascorbic acid), polyhydroxy acids (ie: gluconolactone, lactobionic acid), beta hydroxyl acid, and derivatives and combinations thereof. Exemplary moisturizers include glycerin, dimethicones, triglycerides, natural oils (i.e., olive oil, jojoba oil, soybean oil, coconut oil), silicone, dormin, shea butter, lanolin, glycerides, coco butter, and derivatives and combinations thereof. Exemplary antioxidants include retinol, retinyl palmitate (vitamin A), ascorbic acid (vitamin C), tocopheryl acetate (vitamin E), feverfew, hydroxytyrosol, CoQ10, resveratrol, sirtuins, carotenoids, alpha lipoic acid and derivatives and combinations thereof.

Another preferred skin care composition includes the following materials: water, caprylic/capric triglyceride, Butyrospermum Parkii (shea) butter, cyclopentasiloxane, glycerin, glyceryl stearate, butylene glycol, stearic acid, Carthamus Tinctorius (Safflower) Seed Oil, stearyl alcohol, polysorbate 60, cyclohexasiloxane, sorbitol, dimethicone, dimethicone/vinyl dimethicone crosspolymer, phenoxyethanol, fragrance, caprylyl glycol, retinol, polysorbate 20, ethylhexylglycerin, Glycyrrhiza Glabra (Licorice) Root Extract, BHT, disodium EDTA, dipotassium glycyrrhizate, hexylene glycol, tocopheryl acetate, triethanolamine, carbomer, bisabolol, glyceryl acrylate/acrylic acid copolymer, sodium hyaluronate, and dye.

Another preferred skin care composition includes the following materials: cyclopentasiloxane, isododecane, dimethicone/bis-isobutyl PPG-20 crosspolymer, cyclohexasiloxane, ethoxydiglycol, ascorbic acid, caprylic/capric triglyceride, kojic acid, azelaic acid, ethylhexyl hydroxystearate, polysilicone-11, Syringa Vulgaris (Lilac) Leaf cell culture extract, and maltodextrin.

Methods of Using the Exfoliation Tool and the Selected Skin Care Agents

The exfoliation tool and selected skin care agents can be used to treat any skin surface on a human. Exemplary skin surfaces can include the scalp, the face, neck, and décolletage, and the body, such as the back, arms, legs, hands, feet, chest, stomach, and buttocks. The exfoliation tool and skin care agents can be used to treat sensitive skin such as that found on the face, neck, and décolletage as well as tough skin such as that found on knees, elbows, hands, and feet. Further, the exfoliation tool and selected skin care agents may be used to treat a wide variety of people of all ages, skin colors, and skin types. For example, the exfoliation tool and selected skin care agents can be used to treat people from infants, to children, to teenagers, to adults, and the elderly. The exfoliation tool and selected skin care agents can be used to treat a variety of skin colors including fair, olive, tan, brown, and black, and all of the variations in between. Finally, the exfoliation tool and selected skin care agents can be used to treat a variety of skin types including dry, normal, oily, sensitive, and acne-prone skin, and combinations of these.

The exfoliation tool and selected skin care agents can be used to treat, maintain, or improve a variety of skin care features or ailments such as skin health and integrity, skin healing, scalp irregularities or ailments, and visual or cosmetic irregularities or ailments.

The exfoliation tool and selected skin care agents can be used to maintain skin health by improving the skin integrity and water retention. Healthy skin retains water well compared to dry skin. When the exfoliation tool and selected skin care agents are used as directed for a period of time, the skin should have an improvement in transepidermal water loss (TEWL).

The exfoliation tool and selected skin care agents can be used to maintain a healthy scalp, or treat or improve scalp irregularities and ailments such as dandruff, dry scalp, baldness, hair thinning, and alopecia. The exfoliation tool and selected skin care agents can also be used to improve the health, quality, look or feel of hair by maintaining a healthy scalp, or treating the scalp. For example, the exfoliation tool and selected skin care agents can be used to improve hair texture, hair breakage, hair volume, and hair shine.

Finally, the exfoliation tool and selected skin care agents can be used to maintain healthy skin, or treat or improve skin irregularities and ailments such as scarring, sun damage, fine lines, deep lines or wrinkles, acne, blocked pores, blackheads, dry skin, oily skin, birthmarks, irregular skin tone or color, pore size, stretch marks, uneven texture, age spots, lack of firmness or skin tightness, cellulite, spider veins, fungus, rashes, keritosis pilaris, hair growth in the case of areas where hair growth is undesired, irritation or skin sensitivities, redness, puffiness or bloating, eczema, psoriasis, and rosacea.

In some embodiments, the exfoliation tool and the selected skin care agents can be used as part of a skin care regimen where particular agents are used together with the exfoliation tool. For example, when treating the scalp, it may be beneficial to use the exfoliation tool with at least one agent that is directed to maintaining, treating, or improving scalp health and hair loss such as an antidandruff agent, a cleanser, a moisturizer, or a hair conditioner. Preferred skin care agents for the scalp include minoxidyl, coal tar, salicylic acid, selenium sulfide, sulfur, zinc pyrithione, and their derivatives and combinations. In some embodiments, it may be beneficial to use the exfoliation tool with an agent that is part of a shampoo, conditioner, hair mask, scalp treatment, pre-treatment, or other treatment or tonic composition.

When treating skin on the face, neck, and décolletage, it may be beneficial to use the exfoliation tool with at least one agent that is directed to maintaining, treating, or improving skin health such as an abrasive, antiacne agent, antifungal agent, antimicrobial agent, antioxidant, toner, moisturizer, skin conditioner, humectant, emollient, skin bleaching or lightening agent, protein, or cleanser. Preferred skin care agents for the face, neck, and décolletage include retinol, sericin, hexapeptide-21, myristoyl pentapeptide-8, myristoyl tetrapeptide-8, oligopeptide 10, palmitoyl hexapeptide-14, palmitoyl oligopeptide, palmitoyl tetrapeptide-7, tetrapeptide-16, hyaluronic acid, alpha hydroxyl acids (ie: glycolic acid, lactic acid, ascorbic acid), polyhydroxy acids (ie: gluconolactone, lactobionic acid), beta hydroxyl acid, glycerin, silicone, jojoba oil, dormin, shea butter, dimethicones, olive oil, soybean oil, lanolin, glycerides, coco butter, coconut oil, retinyl palmitate (vitamin A), caffeine, ascorbic acid (vitamin C), tocopheryl acetate (vitamin E), feverfew, hydroxytyrosol, CoQ10, resveratrol, sirtuins, carotenoids, alpha lipoic acid, hydroquinone, benzoyl peroxide, sulfur, salicylic acid, actizyme, and derivatives and combinations of these. In some embodiments, it may be beneficial to use the exfoliation tool with an agent that is part of a cleanser, toner, moisturizer, exfoliant, mask, or serum composition. Similar agents and compositions can be used for treating body skin such as on the arms, legs, hands, feet, back, stomach, and buttocks. The agents and compositions can be used in varying concentrations and potentially higher concentrations on body skin versus the sensitive skin such as the face, neck, and décolletage. Additional preferred skin care agents include calcium undecylenate, ketoconazol, povidone-iodine (PVP-iodine), tea tree oil, undecylenic acid, zinc undecylenate, lower chain ($C_1$-$C_4$) alcohols, quaternary ammonium compounds such as benzalkonium chloride and benzethonium chloride, clindamycin, methylbenzethonium chloride, hydrogen peroxide, phenols, triclosan, povidone-iodine (PVP-Iodine), and their derivatives and combinations.

The following table describes some exemplary method embodiments. This table is designed to be exemplary only and not limiting:

TABLE A

Exemplary Method Embodiments

| Step 1 | Step 2 | Step 3 | Step 4 | Step 5 | Step 6 | Step 7 | Step 8 |
|---|---|---|---|---|---|---|---|
| Face, Neck, and Décolletage Treatment | | | | | | | |
| Cleanser | Exfoliation Tool | | | | | | |
| Exfoliation Tool | Cleanser | | | | | | |
| Cleanser | Toner | Exfoliation Tool | | | | | |
| Cleanser | Exfoliation Tool | Toner | | | | | |
| Cleanser | Toner | Moisturizer | Sunscreen | Exfoliation Tool | | | |
| Cleanser | Toner | Exfoliation Tool | Moisturizer | Sunscreen | | | |
| Cleanser | Toner | Exfoliation Tool | Moisturizer | | | | |
| Cleanser | Toner | Exfoliant | Exfoliation Tool | | | | |
| Cleanser | Toner | Moisturizer | Sunscreen | Cleanser | Toner | Exfoliation Tool | Moisturizer |
| Body Treatment | | | | | | | |
| Cleanser | Exfoliation Tool | | | | | | |
| Exfoliation Tool | Cleanser | | | | | | |
| Cleanser | Exfoliation Tool | Moisturizer | | | | | |
| Cleanser | Exfoliation Tool | Treatment | Moisturizer | | | | |
| Cleanser | Exfoliation Tool | Exfoliant | | | | | |
| Cleanser | Exfoliant | Exfoliation Tool | Moisturizer | | | | |
| Cleanser | Exfoliant | Exfoliation Tool | Moisturizer | Sunscreen | | | |
| Scalp Treatment | | | | | | | |
| Shampoo | Exfoliation Tool | | | | | | |
| Exfoliation Tool | Shampoo | | | | | | |
| Shampoo | Exfoliation Tool | Conditioner | | | | | |
| Pre-Treatment | Shampoo | Exfoliation Tool | Conditioner | | | | |
| Scalp Treatment | Shampoo | Exfoliation Tool | Conditioner | | | | |
| Hair Mask | Exfoliation Tool | Shampoo | Conditioner | | | | |
| Shampoo | Exfoliation Tool | Conditioner | Treatment | | | | |
| Exfoliation Tool | Shampoo | Conditioner | | | | | |
| Exfoliation Tool | Shampoo | Treatment | Conditioner | | | | |

The steps in Table A can be performed in any order. Some steps can be combined into a single skin care composition (such as a combination of moisturizer and sunscreen). Finally, the steps can take place over time. For example, some steps can be performed in the morning and other steps can be performed in the evening. Some steps can be performed daily and other steps can be performed less frequently, such as weekly or monthly.

EXAMPLES

The present disclosure may be better understood with reference to the following example. Thus example is intended to be representative of specific embodiments of the disclosure, and is not intended as limiting the scope of the disclosure.

Example 1

Example 1 determined the effect of the exfoliation tool on skin's water balance, transepidermal water loss (TEWL), corneometry, and skin elasticity. Also evaluated were the visual effects on skin smoothness, softness, and texture. The example compared a skin care regimen of a mask, toner, day cream, serum capsule, and night cream both with and without the use of an exfoliation tool in improving skin appearance.

Thirty female subjects over the age of 35 were enrolled in an 8-week, single site, investigator-blinded study. Twenty subjects used a skin care treatment regimen consisting of a cleansing mask, toner, day cream, serum capsules, and night cream. In addition, these subjects also used an exfoliation tool nightly (every other night for the first 2 weeks, then nightly thereafter). Ten subjects used only the skin care regimen without the exfoliation tool. Investigator assessments, subject assessments, photography, and noninvasive assessments were used to evaluate the effectiveness of the two treatment arms. Subjects were evaluated at the following time points: baseline, 5 minutes, week 2, week 4, and week 8.

Subjects using the exfoliation tool were instructed to use the cleansing mask, toner, and day cream in the morning and use the cleansing mask, toner, exfoliation tool, serum capsules, and night cream in the evening in that order. Subjects that did not use the exfoliation tool followed the same protocol but did not use the exfoliation tool in the evening.

Subject were given the following directions for the products and the exfoliation tool if applicable:

Product 1 Cleansing Mask:

Using wet fingertips, gently and evenly massage a quarter-sized amount onto dry skin. Ensure entire face is covered with a thin coat of product, avoiding contact with eyes. Allow product to dry completely, about 2-3 minutes. Rinse thoroughly; pat dry.

Product 2 Toner:

Shake well before use. Apply evenly to entire face with a gauze pad, avoiding the eye area. Do not rinse off. Allow to dry.

Product 3 Day Cream SPF 30:

Apply a dime-sized amount over entire face every morning. Avoid eye area.

Product 4 Serum Capsules:

Open capsule and apply serum to the entire face evenly. Use only in the evening.

Product 5 Night Cream:

Apply a dime-sized amount over entire face every evening.

Exfoliation Tool:

For Week 1 and Week 2, use tool every other night after Products 1 and 2. For Weeks 3-8, increase to nightly use as tolerated. With moderate and comfortable pressure, roll the tool over entire face and neck 4-10 times. For best results, divide the face into sections (forehead, right side, left side, chin, neck) and treat each section before continuing onto the next. Change the orientation of rolling over each section to ensure complete surface coverage. After rolling, apply Product 4 (one Serum Capsule) over entire face and neck and follow with Product 5 (Night Cream).

Subjects were evaluated by collecting observations at baseline, 5 minutes, week 2, week 4, and week 8. A dermatologist investigator performed all visual assessments. The parameters evaluated consisted of: investigator evaluations, subject evaluations, subject marketing questionnaire, noninvasive assessments (TEWL, corneometry, elasticity), and photography. The rating scale for evaluation for all subject and investigator assessments was: 0=none, 1=minimal, 2=mild, 3=moderate, 4=severe.

After the 8-week study, the following results or observations were made:

The corneometry difference from baseline showed that there was no statistically significant benefit in skin moisturization with the exfoliation tool in addition to the skin care products versus using the skin care products alone. Corneometry is a measure of the conductivity of the skin utilizing water as the conductor. More water in the skin indicates superior hydration, thus a higher corneometry measurement is more favorable.

Both groups (with and without the exfoliation tool) showed a statistically significant improvement in skin moisturization at weeks 2, 4, and 8. This finding points to the ability of the skin care regimen to significantly improve skin moisturization. It is worthwhile noting that the addition of the exfoliation tool to the skin care products produced highly statistically significant (p<0.001) improvement in moisturization at weeks 2 and 4, which was not the case with the skin care product alone group.

The corneometry numbers were noticeably higher in the group that used the exfoliation tool, especially at week 4. This might directionally point to the value of the exfoliation tool in improving skin hydration.

The investigator noted improvements within both groups over the 8 weeks. At week 2, the investigator noted a statistically significant improvement in skin texture in all subjects. A statistically significant improvement was seen in fine lines, skin texture, and overall appearance with both groups at week 4. Finally, at week 8, statistically significant improvement was seen in fine lines, skin texture, and overall appearance. Thus, the skin care regimen was successful in improving skin appearance.

The investigator direct comparison did not show any statistically significant differences between the exfoliation tool plus skin care products and the skin care products group alone. This could be due to the small sample size or the short study period. It is possible that new collagen production from the exfoliation tool might take longer than 12 weeks.

No changes in skin elasticity were seen between the exfoliation tool plus skin care product group and the skin care product group alone. Skin elasticity is more variable in its interpretation than the corneometry measurements. Three elasticity measurements were obtained. The elasticity measurements were obtained with a suction cup that stretched the skin into the cup under negative vacuum pressure. Once the skin was stretched into the top of the cup, such that a light beam at the top of the cup was broken, the negative vacuum pressure was discontinued and the skin relaxed. This sequence of events was repeated three times. With each subsequent iteration of the suction and relaxation, the skin becomes stretchier and stretchier and the numbers decreased. Thus, the skin becomes more elastic with stretching.

There was no intragroup difference in skin elasticity between the exfoliation tool plus skin care product group and the skin care product group alone. However, it is important to look at the absolute numbers, since the sample size was small. The skin elasticity numbers were higher in the exfoliation tool group than in the skin treatment alone group. This means that it took more energy to deform the skin of the subjects that used the exfoliation tool, which can be interpreted as firmer skin possibly due to a higher water content.

No statistically significant differences in skin elasticity were seen on direct comparison between the exfoliation tool plus skin care products and skin care products alone group. Again, it is important to note that the elasticity measurements were higher at week 8 in the group that used the exfoliation tool plus the skin care products. This means that the exfoliation tool improved skin firmness directionally.

The subject difference from baseline was used to analyze intergroup changes. No statistically significant changes were seen between subject assessments in the exfoliation tool plus skin care products group or the skin care products alone group at weeks 2, 4, or 8.

The intragroup longitudinal assessment demonstrated that while both groups of subjects assessed improvement, the improvement was rated more dramatic in the group that used the exfoliation tool and skin care products as opposed to the skin care products alone group. At week 2, there was a statistically significant improvement in skin softness (p=0.032), skin radiance (p=0.008), skin evenness (p=0.002), pore appearance (p=0.012), wrinkles (p=0.006), fine lines (p=0.009), and brown spots (p=0.009). This is improvement in more attributes than the skin care product alone group. Statistically significant improvement was seen in softness, radiance, pores, fine lines, and brown spots with the exfoliation tool at week 2, which was not the case with the skin care products alone. However, the skin care products also elicited excellent ratings by the subjects. There was statistically significant improvement in evenness (p=0.011) and wrinkles (p=0.022) at week 2. By week 4, there was statistically significant improvement in both groups in terms of radiance, evenness, pores, and wrinkles. At week 4, the exfoliation tool plus product group outperformed the product group alone with additional statistically significant improvement in fines lines (p<0.001), brown spots (p<0.001), and dryness (p=0.047). The subject assessed differences were the greatest at week 8. The exfoliation tool group assessed statistically significant improvements in radiance, evenness, pore appearance, wrinkles, fine lines, brown spots, and dryness. No statistically significant increase in irritation was noted pointing toward an excellent tolerability profile for the exfoliation tool. The subjects who used the skin care products alone assessed statistically significant improvement in radiance and evenness. This means that the use of the exfoliation tool added an incremental benefit in pore appearance, wrinkles, fine lines, brown spots and dryness.

The direct comparison results were similar to the difference from baseline results and failed to show much statistically significant intergroup difference. It appears that with the study design and small sample size, the longitudinal analysis was best able to elicit the subtle differences between the two study groups.

No statistically significant differences in TEWL were seen between the exfoliation tool plus study products group and the study products alone group.

TEWL is a measure of the water leaving the skin. Indeed, TEWL was increased in the group using the exfoliation tool. This means that the exfoliation tool did penetrate the skin barrier and allow more water to escape. A statistically significant increase in water loss was seen with the exfoliation tool users as compared to baseline at week 2 (p=0.032) and week 4 (p=0.013). The change was not statistically significant at week 8. No statistically significant changes in TEWL were seen in the product use alone group. The TEWL evaluation demonstrates the ability of the exfoliation tool to produce a physiologic effect on the skin.

No statistically significant differences in TEWL were seen in the intergroup direct comparison analysis. This means that the exfoliation tool did not damage the skin in a negative fashion.

The above specification, examples and data provide a complete description of the use of the disclosed methods and skin care agents. Since many embodiments can be made without departing from the spirit and scope of the disclosure, the invention resides in the claims.

We claim:

1. A method of skin treatment comprising:
   (a) treating the skin with an exfoliation tool, wherein the exfoliation tool comprises a handle and a head, the head comprising a roller, a collar, and a plurality of steel acupuncture needles located on the roller; and thereafter
   (b) applying a first skin care composition to skin, the skin care composition comprising myristoyl pentapeptide-8 or myristoyl tetrapeptide-8; and
   (c) applying a second skin care composition to the skin, wherein the second skin care composition is different from the first skin care composition.

2. A method of skin treatment comprising:
   (a) treating the skin with an exfoliation tool, wherein the exfoliation tool comprises a handle and a head, the head comprising a roller, a collar, and a plurality of steel acupuncture needles located on the roller; and thereafter
   (b) applying a first skin care composition to skin, the skin care composition comprising:
      i) myristoyl pentapeptide-8 or myristoyl tetrapeptide-8 and an optional peptide selected from the group consisting of sericin, silk protein, collagen, keratin, amino acids, hexapeptide-21, oligopeptide 10, palmitoyl hexapeptide-14, palmitoyl oligopeptide, palmitoyl tetrapeptide-7, tetrapeptide-16, arginine, lysine, betaine, milk solids, rice peptides, and derivatives and combinations thereof;
      ii) at least one skin conditioner selected from the group consisting of hyaluronic acid, alpha hydroxyl acids, glycolic acid, lactic acid, ascorbic acid, polyhydroxy acids, gluconolactone, lactobionic acid, beta hydroxyl acid, peat extract, arginine, glycine, and derivatives and combinations thereof;
      iii) at least one moisturizer selected from the group consisting of butylene glycol, propylene glycol, ethoxydigycol, hydroxyethyl urea, glycerin, triglycerides, natural oils, olive oil, jojoba oil, soybean oil, soy, coconut oil, silicone, shea butter, dimethicones, lanolin, coco butter, avocado, bisabolol, ceramide, panthenol, lecithin, tea tree oil, and derivatives and combinations thereof; and
      iv) at least one antioxidant selected from the group consisting of retinol, BHT, tetrahexyldecyl ascorbate, ascorbyl palmitate, retinyl palmitate (vitamin A), ascorbic acid (vitamin C), tocopheryl acetate (vitamin E), feverfew, hydroxytyrosol, CoQ10, resveratrol, carotenoids, alpha lipoic acid, and derivatives and combinations thereof, and
   (c) applying a second skin care composition to the skin, wherein the second skin care composition is different from the first skin care composition.

3. The method of claim 2, wherein the needles on the exfoliation tool are from about 0.1 mm to about 0.5 mm in length.

4. The method of claim 2, wherein the second skin care composition is applied to skin before treating the skin with the exfoliation tool.

5. The method of claim 2, wherein the second skin care composition is applied to skin after treating the skin with the exfoliation tool.

6. The method of claim 2, wherein the acupuncture needles are made of stainless steel.

* * * * *